(12) United States Patent
Diehl et al.

(10) Patent No.: US 8,618,182 B2
(45) Date of Patent: Dec. 31, 2013

(54) PROCESS FOR SYNTHESIZING C5+ HYDROCARBONS IN THE PRESENCE OF A CATALYST PREPARED USING AT LEAST ONE CYCLIC OLIGOSACCHARIDE

(75) Inventors: Fabrice Diehl, Lyons (FR); Anne Griboval-Constant, Villeneuve d'Ascq (FR); Andrei Khodakov, Croix (FR); Alan Jean-Marie, Sangatte (FR); Eric Monflier, La Madeleine (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 0 days.

(21) Appl. No.: 13/812,701

(22) PCT Filed: Jun. 24, 2011

(86) PCT No.: PCT/FR2011/000369
§ 371 (c)(1),
(2), (4) Date: Apr. 4, 2013

(87) PCT Pub. No.: WO2012/013866
PCT Pub. Date: Feb. 2, 2012

(65) Prior Publication Data
US 2013/0184361 A1    Jul. 18, 2013

(30) Foreign Application Priority Data
Jul. 29, 2010   (FR) ..................................... 10 03186

(51) Int. Cl.
*C07C 27/00* (2006.01)

(52) U.S. Cl.
USPC .......................................... 518/700; 518/715

(58) Field of Classification Search
USPC .................................................. 518/700, 715
See application file for complete search history.

(56) References Cited

U.S. PATENT DOCUMENTS

| 5,856,261 A | 1/1999 | Culross et al. |
|---|---|---|
| 2005/0040090 A1 | 2/2005 | Wang et al. |
| 2012/0048777 A1* | 3/2012 | Derr et al. ................ 208/120.01 |

OTHER PUBLICATIONS

International Search Report of International Application No. PCT/FR2011/000369, Jan. 2013.

* cited by examiner

*Primary Examiner* — Jafar Parsa
(74) *Attorney, Agent, or Firm* — Millen, White, Zelano & Branigan, P.C.

(57) ABSTRACT

C5+ hydrocarbon synthesis by contracting a synthesis gas with a catalyst naming at least one metal from group VIII deposited on a support formed by at least one oxide, said catalyst being prepared using a process of at least:
i) contracting at least the support with at least one solution containing at least one precursor of metal from group VIII;
ii) contracting at least the support with at least one organic compound formed from at least one cyclic oligosaccharide composed of at least 6 α-(1,4)-bonded glucopyranose sub-units;
iii) at least one calcining to obtain at least the metal from group VIII in the oxide form;
i) and ii) being carried out separately, in any order, or simultaneously.

15 Claims, No Drawings

PROCESS FOR SYNTHESIZING C5+ HYDROCARBONS IN THE PRESENCE OF A CATALYST PREPARED USING AT LEAST ONE CYCLIC OLIGOSACCHARIDE

FIELD OF THE INVENTION

The present invention relates to the field of Fischer-Tropsch synthesis processes which can be used to produce a wide range of hydrocarbon cuts from a mixture of CO+$H_2$, generally known as synthesis gas or syngas.

The simplified stoichiometric equation (limited in the equation below to the formation of alkanes) for the Fischer-Tropsch synthesis is written as:

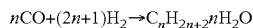

$$nCO+(2n+1)H_2 \rightarrow C_nH_{2n+2} nH_2O$$

This reaction is generally carried out at medium or high temperature and under pressure.

EXAMINATION OF THE PRIOR ART

The catalysts used for Fischer-Tropsch synthesis are usually supported catalysts based on alumina, silicated alumina, silica-alumina, silica, titanium dioxide, zirconia or combinations of such supports, the active phase principally being constituted by iron (Fe) or cobalt (Co) optionally doped with a noble metal such as Pt, Rh or Ru.

The skilled person is well aware that the preparation of catalysts for Fischer-Tropsch synthesis using conventional methods, for example dry impregnation, results in catalysts with a mean metal oxide size, particularly of cobalt oxide ($Co_3O_4$), which is often high and poorly controlled (large disparity of sizes of metal oxide crystallites, particularly crystallites of cobalt oxide, $Co_3O_4$). This results in catalysts with a mediocre catalytic activity for Fischer-Tropsch synthesis, the catalytic performances of which might vary depending on the degree of aggregation of the metal, particularly cobalt.

Many studies have been carried out with the aim of increasing the dispersion of the metal, in particular cobalt, present in the active phase of Fischer-Tropsch synthesis catalysts in order to obtain more active catalysts. To this end, the introduction of an organic compound during the preparation of the catalyst has frequently been recommended. In particular, patents U.S. Pat. No. 5,856,260 and U.S. Pat. No. 5,856,261 respectively disclose introducing, during preparation of the catalyst, polyols with general formula $C_nH_{2n+2}O_x$ with n being a whole number in the range 2 to approximately 6, and x a whole number in the range 2 to 11 or sugars of the mono- or disaccharide type, with sucrose being particularly preferred. Patent application US 2005/0026776 discloses the use of chelating compounds of the nitriloacetic acid (NTA), trans-1,2-cyclohexadiamine-N,N,N',N' tetraacetic acid (CyDTA) or ethylenediaminetetraacetic acid (EDTA) type, or glycine, aspartic acid or citric acid, in order to obtain a catalyst with a reduced $Co_3O_4$ crystallite size. Patent application US 2002/0082166 discloses the use of a solution containing an organo-ammonium derivative with formula $R_1R_2R_3R_4N$—OH (in which $R_1$ to $R_4$ are hydrocarbon chains or hydrogen atoms) or ammonium hydroxide, $NH_4OH$, to obtain a Fischer-Tropsch catalyst based on cobalt which is more active and more selective for heavy products.

Despite improvements to catalysts used for Fischer-Tropsch synthesis, these have only rarely resulted in optimized catalytic performances, especially in terms of catalytic activity. Thus, the present invention proposes providing a novel hydrocarbon synthesis process resulting in improved performances over those obtained with catalysts prepared in accordance with previous methods.

SUMMARY AND ADVANTAGE OF THE INVENTION

The present invention provides a process for synthesizing essentially linear, saturated C5+ hydrocarbons, consisting of bringing a feed comprising synthesis gas into contact with at least one catalyst the active phase of which comprises at least one metal from group VIII deposited on a support formed by at least one oxide, said catalyst being prepared using a process comprising at least:

i) at least one step for bringing at least said support into contact with at least one solution containing at least one precursor of said metal from group VIII;
ii) at least one step for bringing at least said support into contact with at least one organic compound formed from at least one cyclic oligosaccharide composed of at least 6 α-(1,4)-bonded glucopyranose subunits;
iii) at least one calcining step to obtain at least said metal from group VIII in the oxide form;

the steps i) and ii) possibly being carried out separately, in any order, or simultaneously.

In accordance with the synthesis process of the invention, said metal from group VIII present in the active phase of the catalyst is preferably cobalt. It is advantageous to use a catalyst the active phase of which is formed from two metals, preferably cobalt and platinum.

In accordance with the synthesis process of the invention, said catalyst is preferably prepared in the presence of a cyclodextrin as the organic compound.

Surprisingly, it has been discovered that a catalyst the active phase of which comprises at least one metal from group VIII, particularly cobalt, and prepared in the presence of at least one organic compound formed from at least one cyclic oligosaccharide composed of at least 6 α-(1,4)-bonded glucopyranose subunits, preferably a cyclodextrin, has a dispersion of said metal from group VIII which is substantially superior to that presented by catalysts prepared in the absence of a cyclic oligosaccharide due to a reduction in the size (diameter) of the crystallites of an oxide of the metal from group VIII present in the active phase of the catalyst. This results in the presence of a larger number of active sites for the catalysts prepared in the presence of at least one cyclic oligosaccharide composed of at least 6 α-(1,4)-bonded glucopyranose subunits. When employed in a Fischer-Tropsch synthesis process, such catalysts, prepared in the presence of at least one cyclic oligosaccharide composed of at least 6 α-(1,4)-bonded glucopyranose subunits results in improved catalytic performances in terms of catalytic activity and productivity as regards the desired C5+ hydrocarbon products.

DESCRIPTION OF THE INVENTION

The present invention concerns a process for synthesizing essentially linear, saturated C5+ hydrocarbons consisting of bringing a feed comprising synthesis gas into contact with at least one catalyst the active phase of which comprises at least one metal from group VIII deposited on a support formed by at least one oxide, said catalyst being prepared using a process comprising at least:

i) at least one step for bringing at least said support into contact with at least one solution containing at least one precursor of said metal from group VIII;

ii) at least one step for bringing at least said support into contact with at least one organic compound formed from at least one cyclic oligosaccharide composed of at least 6 α-(1,4)-bonded glucopyranose subunits;

iii) at least one calcining step to obtain at least said metal from group VIII in the oxide form;

the steps i) and ii) possibly being carried out separately, in any order, or simultaneously.

The process of the invention results in the production of essentially linear, saturated C5+ hydrocarbons. In accordance with the invention, the term "essentially linear, saturated C5+ hydrocarbons" means hydrocarbons for which the proportion of hydrocarbon compounds containing at least 5 carbon atoms per molecule represents at least 50% by weight, preferably at least 80% by weight of the total of the hydrocarbons formed, the quantity of olefinic compounds present in said hydrocarbon compounds containing at least 5 carbon atoms per molecule being less than 10% by weight. The hydrocarbons produced by the process of the invention are thus essentially paraffinic hydrocarbons, wherein the fraction having the highest boiling points may be converted in high yield to middle distillates (gas oil and kerosene cuts) by a hydroconversion process such as catalytic hydrocracking and/or hydroisomerization.

The feed employed to carry out the process of the invention comprises, and is preferably constituted by, synthesis gas. Synthesis gas is a mixture of carbon monoxide and hydrogen with $H_2/CO$ molar ratios which can vary from 0.5 to 4 as a function of the process via which it has been obtained. The $H_2/CO$ molar ratio of synthesis gas is generally close to 3 when the synthesis gas is obtained from a process for steam reforming hydrocarbons or alcohol. The $H_2/CO$ molar ratio of synthesis gas is of the order of 1.5 to 2 when the synthesis gas is obtained from a partial oxidation process. The $H_2/CO$ molar ratio of synthesis gas is generally close to 2.5 when it is obtained from a thermal reforming process. The $H_2/CO$ molar ratio of synthesis gas is generally close to 1 when it is obtained from a $CO_2$ gasification and reforming process.

The catalyst used in the hydrocarbon synthesis process of the invention may be employed in different types of reactors, for example in a fixed bed, moving bed, ebullated bed or a three-phase fluidized bed. Preferably, the catalyst is used in suspension in a three-phase fluidized reactor, preferably of the bubble column type. In this preferred use of the catalyst, said catalyst is divided into a very fine powder, particularly of the order of a few tens of microns, said powder forming a suspension with the reaction medium. This technique is also known to the skilled person as a "slurry" process.

The catalyst employed to carry out the hydrocarbon synthesis process of the invention comprises an active metallic phase deposited on a support, said active phase comprising at least one metal from group VIII preferably selected from cobalt, nickel, ruthenium and iron. In the case in which the active phase comprises at least one metal selected from cobalt, nickel and iron, the quantity of said metal represents 1% to 60% by weight with respect to the weight of catalyst, preferably 5% to 30% by weight with respect to the weight of catalyst and highly preferably 10% to 30% by weight with respect to the weight of catalyst. In the case in which the active phase comprises ruthenium, the quantity of ruthenium is in the range 0.01% to 10% by weight with respect to the weight of the catalyst and highly preferably in the range 0.05% to 5% by weight with respect to the weight of the catalyst. Said active phase deposited on said support advantageously comprises a metal selected from cobalt, nickel, ruthenium and iron or a plurality of metals selected from cobalt, nickel, ruthenium and iron. Highly preferably, said active phase comprises cobalt. The active phase of said catalyst also advantageously comprises at least one additional metal selected from platinum, palladium, rhenium, ruthenium, manganese and tantalum and highly preferably selected from platinum, ruthenium and rhenium. Said additional metal(s) is (are) preferably present in a quantity of 0.01% to 2% by weight, preferably 0.03% to 0.5% by weight with respect to the weight of the catalyst.

Prior to carrying out the process of the invention, the catalyst is preferably in the oxide form. It contains reduced sized crystallites of the oxide of said metal from group VIII, present in the active phase of said catalyst, preferably crystallites of cobalt oxide $Co_3O_4$, encouraging optimized dispersion of said metal from group VIII present in the active phase of said catalyst. Preferably, said crystallites of the oxide of the metal from group VIII have a mean diameter of at least 6 nm. Preferably, the mean diameter of said crystallites of the oxide of a metal from group VIII does not exceed 50 nm, and highly preferably, it does not exceed 30 nm or even 20 nm; still more preferably, it does not exceed 15 nm. The mean size (mean diameter) of crystallites of at least said metal from group VIII present in the active phase of the catalyst is a parameter which characterizes the dispersion of said metal from group VIII present in the active phase of said catalyst, preferably cobalt. The mean size of the crystallites of at least said metal from group VIII present in the active phase of the catalyst is determined by X ray diffraction using the Scherrer equation for the diffraction peak attributed to said metal from group VIII. In the preferred case where said metal from group VIII is cobalt, the mean size of the crystallites of cobalt oxide is determined by X ray diffraction using the Scherrer equation on the diffraction peak at 59.5° (511 plane) (principal diffraction peak for $Co_3O_4$). The dispersion of said metal from group VIII present in the active phase of the catalyst, in particular the dispersion of cobalt, may also be estimated by a propene chemisorption method such as that described in the publication by A S Lermontov, J S Girardon, A Griboval-Constant, D Pietrzyk and A Y Khodakov, Catalysis Letters 101 (2005), 117.

The support on which said active phase is deposited is advantageously formed from at least one simple oxide selected from alumina ($Al_2O_3$), silica ($SiO_2$), titanium oxide ($TiO_2$), cerine ($CeO_2$) and zirconia ($ZrO_2$). It may also advantageously be formed from a plurality of simple oxides selected from alumina ($Al_2O_3$), silica ($SiO_2$), titanium oxide ($TiO_2$), cerine ($CeO_2$) and zirconia ($ZrO_2$); highly preferably, said support is formed from silica and alumina. The alumina phase present in a support constituted by silica-alumina is a transition alumina formed from at least one δ, γ, θ or α crystallographic phase. Such a support constituted by silica-alumina preferably comprises 1% to 30% of silica. Said silica-alumina is homogenous on the micrometric scale, and more preferably homogenous on the nanometric scale. The support on which said active phase is deposited may also advantageously be formed from a spinel included in an alumina or a silica-alumina, preferably in a silica-alumina. In particular, said catalyst support may advantageously be constituted by a simple spinel, included in a silica-alumina, of the type $MAl_2O_4/Al_2O_3.SiO_2$ or a mixed spinel, included in a silica-alumina, of the type $M_xM'_{(1-x)}Al_2O_4/Al_2O_3.SiO_2$ where M and M' are distinct metals selected from the group constituted by magnesium (Mg), copper (Cu), cobalt (Co), nickel (Ni), tin (Sn) zinc (Zn), lithium (Li), calcium (Ca), caesium (Cs), sodium (Na), iron (Fe) and manganese (Mn), where "$Al_2O_3.SiO_2$" denotes the chemical formula of a silica-alumina, where x is in the range 0 to 1, the values 0 and 1 being excluded. Such a support formed from a spinel structure comprises at least 5% by weight of said spinel structure, preferably at least 10% by weight, and more preferably at least 15% by weight. The silica-alumina in which the spinel structure is preferably included preferably comprises 1% to 30% by weight of silica. It is homogenous on the micrometric scale, and more preferably, homogenous on the nanometric scale.

A support formed from a spinel included in an alumina or a silica-alumina may be prepared using any method known to the skilled person. In particular, any process that can obtain said support, modified by addition of at least one element M to obtain a simple spinel structure and at least one element M' to obtain a mixed spinel structure, is suitable. An example of a method for the preparation of such a support consists of impregnating an alumina or silica-alumina support, preformed or as a powder, with at least one aqueous solution containing hydrosoluble precursors of the elements selected for the spinel structure and generally to carry out steps of washing, drying and finally calcining. Another method consists of preparing said catalyst support based on alumina or silica-alumina by co precipitation of an aqueous solution containing the metals Al, M and optionally M', for example in the form of nitrates, by an aqueous alkaline carbonate or bicarbonate solution, followed by washing, drying, and finally calcining. Another method consists of preparing said catalyst support based on alumina or silica-alumina by the sol-gel process, or by complexing an aqueous solution containing the metals Al, M and optionally M' by at least one alpha alcohol acid added in an amount of 0.5 to 2 moles of acid per mole of metals, followed by drying under vacuum to produce a homogenous vitreous substance, then by calcining. These methods for the preparation of such a support to obtain a spinel included in an alumina or a silica-alumina are well known to the skilled person. Such a support undergoes a heat treatment before the preparation proper of the catalyst used in the process of the invention in order to obtain the spinel structure (M aluminate or M and M' aluminate, where M and M' have the definitions given above). Said heat treatment is preferably carried out at a temperature in the range 600° C. to 1200° C., highly preferably in the range 740° C. to 1030° C. and still more preferably in the range 800° C. to 980° C. It is carried out in an oxidizing atmosphere, for example in air or in air depleted in oxygen. It may also be carried out at least partially under nitrogen.

The support on which said active phase is deposited may have a morphology in the form of beads, extrudates (for example trilobes), or pellets, especially when said catalyst is used in a fixed bed reactor, or it has a morphology in the form of a powder with a variable grain size, especially when said catalyst is used in a slurry bubble column. The grain size of the catalyst may be in the range from a few microns to a few hundred microns. For "slurry" reactors, the particle size of the catalyst is preferably in the range 10 microns to 500 microns, preferably in the range 10 microns to 300 microns, more preferably in the range 20 to 200 microns, and still more preferably in the range 30 to 160 microns.

The catalyst used in the hydrocarbon synthesis process of the invention is prepared using a process comprising at least:
i) at least one step for bringing at least said support into contact with at least one solution containing at least one precursor of said metal from group VIII;
ii) at least one step for bringing at least said support as described above into contact with at least one organic compound formed from at least one cyclic oligosaccharide composed of at least 6 α-(1,4)-bonded glucopyranose subunits;
iii) at least one calcining step to obtain at least said metal from group VIII in the oxide form;

the steps i) and ii) possibly being carried out separately, in any order, or simultaneously.

Deposition of at least said metal from group VIII on said support in accordance with the implementation of said step i) may be carried out using any method well known to the skilled person. Said step i) is preferably carried out by impregnation of the support using at least one solution containing at least one precursor of said metal from group VIII. In particular, said step i) may be carried out by dry impregnation, excess impregnation, or by deposition-precipitation (as described in patents U.S. Pat. No. 5,874,381 and U.S. Pat. No. 6,534,436) using methods which are well known to the skilled person. Preferably, said step i) is carried out by dry impregnation, which consists of bringing the catalyst support into contact with a solution containing at least one precursor of said metal from group VIII the volume of which is equal to the pore volume of the support to be impregnated. This solution contains metallic precursors of the metal from group VIII or metals in the desired concentration.

Said metal(s) from group VIII is (are) brought into contact with said support using any metallic precursor which is soluble in an aqueous phase or an organic phase. When it is introduced in organic solution, said precursor of the metal from group VIII is, for example, the oxalate or acetate of said metal from group VIII. Preferably, said precursor of the metal from group VIII is introduced in aqueous solution, for example in the form of a nitrate, carbonate, acetate, chloride or oxalate, complexes formed by a polyacid or an acid-alcohol and its salts, complexes formed with acetylacetonates, or any other inorganic derivative which is soluble in aqueous solution, which is brought into contact with said support. In the preferred case in which said metal from group VIII is cobalt, the cobalt precursor is advantageously cobalt nitrate, cobalt oxalate or cobalt acetate.

Contact of said organic compound used to carry out said step ii) with said support is carried out by impregnation, in particular by dry impregnation or excess impregnation, preferably by dry impregnation. Said organic compound is preferably impregnated onto said support after dissolving into aqueous solution.

Said organic compound is formed from at least one cyclic oligosaccharide composed of at least 6 α-(1,4)-bonded glucopyranose subunits. A spatial representation of a glucopyranose subunit is given below:

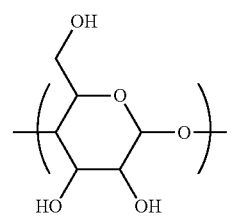

Said organic compound is preferably selected from cyclodextrins, substituted cyclodextrins, polymerized cyclodextrins and mixtures of cyclodextrins. Cyclodextrins are a family of cyclic oligosaccharides composed of α-(1,4)-bonded glucopyranose subunits. They are cage molecules. In accordance with the invention, preferred cyclodextrins are α-cyclodextrin, β-cyclodextrin and γ-cyclodextrin respectively composed of 6, 7 and 8 α-(1,4)-bonded glucopyranose subunits. Developed representations of α-cyclodextrin, β-cyclodextrin and γ-cyclodextrin are given below. Preferably, to carry out said step ii), β-cyclodextrin is used, composed of 7 α-(1,4)-bonded glucopyranose subunits. Cyclodextrins are commercially available compounds.

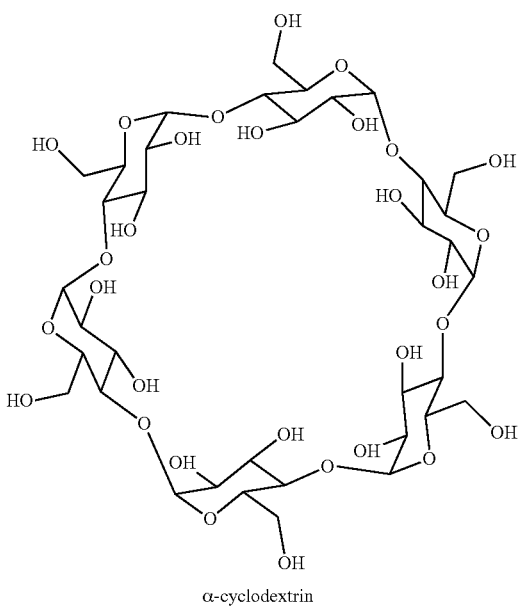

α-cyclodextrin

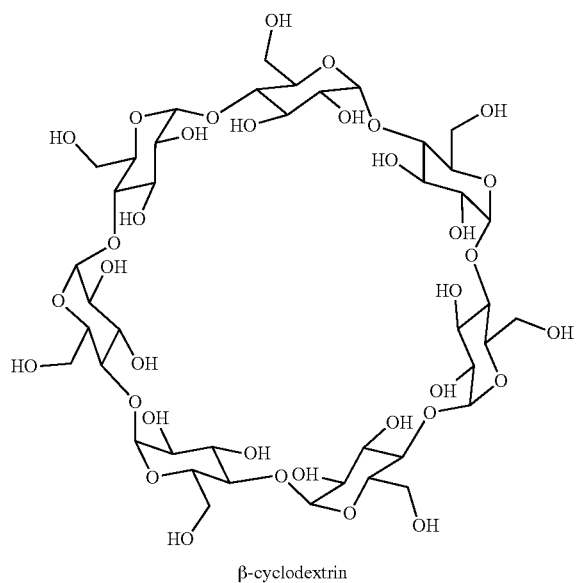

β-cyclodextrin

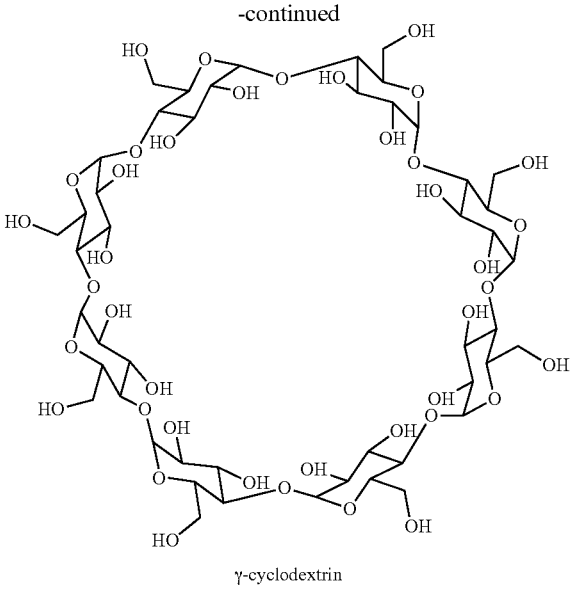

γ-cyclodextrin

The substituted cyclodextrins advantageously employed to carry out said step ii) are constituted by 6, 7 or 8 α-(1,4)-bonded glucopyranose subunits, wherein at least one is mono- or polysubstituted. The substituents may be attached to one or more hydroxyl group(s) present in the molecule, namely to hydroxyl groups bonded directly to the cycle of a glucopyranose unit and/or to the hydroxyl bonded to the $CH_2$ group itself bonded to the cycle of a glucopyranose unit. More preferably, said substituted cyclodextrins carry one or more substituents, which may be identical or different, selected from saturated or unsaturated alkyl radicals, which may or may not be functionalized, and ester, carbonyl, carboxyl, carboxylate, phosphate, ether, polyether, urea, amide, amine, triazole or ammonium functions. Preferred substituted cyclodextrins are methylated, ethylated, propylated and allyl (i.e. having a function with the semi-developed formula —$CH_2$—CH═$CH_2$) cyclodextrins, succinylated (i.e. having a function with the semi-developed formula R—OCO—$CH_2$—$CH_2$COOH) cyclodextrins, carboxylated, carboxymethylated, acetylated, 2-hydroxpropylated and polyoxyethylenated cyclodextrins. The cyclodextrin mono- or poly-substituents may also be a monosaccharide or disaccharide molecule such as a molecule of maltose, glucose, fructose or saccharose.

Particularly advantageous substituted cyclodextrins for carrying out said step ii) are hydroxypropyl beta-cyclodextrin and methylated beta-cyclodextrins.

The polymerized cyclodextrins which are advantageously employed for carrying out said step ii) are polymers wherein the monomers are each constituted by a cyclic oligosaccharide composed of 6, 7 or 8 α-(1,4)-bonded glucopyranose subunits, which may or may not be substituted. A cyclodextrin in the polymerized form, cross-linked or not, which may advantageously be used to carry out said step ii) is, for example, of the type obtained by polymerization of monomers of beta-cyclodextrin with epichlorhydrin or a polyacid.

Advantageous mixtures of cyclodextrins employed in carrying out said step ii) employ substituted or unsubstituted cyclodextrin. Said mixtures could, for example, contain each of the three types of cyclodextrins (alpha, beta and gamma) jointly and in varying proportions.

Introduction of said organic compound, preferably a cyclodextrin and highly preferably beta-cyclodextrin, for carrying out said step ii) is such that the molar ratio {(metal(s) from group VIII in the oxide form present in the active phase of the catalyst obtained at the end of said step iii)/organic compound} is in the range 10 to 300, preferably in the range 50 to 180. The metals from group VIII taken into account for the calculation of said molar ratio are the metals introduced to carry out said step i) are in the oxide form in the active phase of the catalyst obtained from said step iii). As a result, said metal(s) from group VIII can be reduced: they will be reduced prior to using them in the hydrocarbon synthesis process of the invention. In particular, the calculation of said molar ratio of the quantity of metal from group VIII which may be present in a spinel structure (metal M or M' as defined above in the present description) employed as the component of the catalyst support is not taken into account.

The hydrocracking catalyst preparation process employed in the hydrocracking process of the invention includes several implementations.

A first implementation consists of carrying out said steps i) and ii) simultaneously such that said organic compound, preferably a cyclodextrin, and at least said precursor of at least said metal from group VIII present in the active phase are co-impregnated onto said support (co-impregnation step). Said first implementation advantageously comprises carrying out one or more steps i). In particular, one or more steps i) advantageously precede and/or follow said co-impregnation step. In accordance with said first implementation, each of the steps carried out is preferably followed immediately by at least one step for drying then at least one calcining step. In particular, said co-impregnation step is followed by at least one drying step then at least one calcining step. Said first implementation may comprise several co-impregnation steps. Said calcining step iii) is at least carried out when all of the steps for depositing at least said metal from group VIII onto the catalyst support have been carried out.

A second implementation consists of carrying out said step i) prior to said step ii). In accordance with said second implementation, one or more steps i) for depositing at least said metal from group VIII present in the active phase of the catalyst precede(s) said step ii). Preferably, each of said steps i) is followed immediately by at least one drying step and at least one calcining step. In particular, the last step i) is advantageously followed by at least one drying step and at least one calcining step in accordance with said step iii) before carrying out said step ii). Said step ii) is advantageously followed by at least one drying step and optionally at least one calcining step.

A third implementation consists of carrying out said step ii) prior to said step i). Said step ii) is preferably followed immediately by at least one drying step and optionally by at least one calcining step before carrying out said step i). Advantageously, said step ii) is followed by several steps i). Preparation of the catalyst in accordance with said third implementation is advantageously terminated by said calcining step iii).

Each of the three implementations described above may be carried out independently such that the catalyst used in the process of the invention is prepared either in accordance with said first implementation or in accordance with said second implementation or in accordance with said third implementation. However, it may be advantageous to associate said first implementation with said second implementation or with said third implementation: thus, both the metal from group VIII present in the active phase and the organic compound, preferably a cyclodextrin, are deposited in at least two events on the catalyst support, namely at least once by co-impregnation and at least once by successive impregnation.

The drying steps carried out to prepare the catalyst prepared in accordance with at least one implementation described above are carried out at a temperature in the range 80° C. to 160° C. They are preferably carried out for a period in the range 1 to 4 hours. Said calcining step iii) is carried out at a temperature in the range 200° C. to 800° C., preferably in the range 250° C. to 600° C. and more preferably in the range 300° C. to 430° C. It is preferably carried out for a period in the range 2 to 6 hours. The calcining steps carried out to prepare the catalyst prepared in accordance with at least one implementation described above are advantageously carried out under the same conditions as said step iii).

The preparation of the catalyst used in the hydrocarbon synthesis process of the invention advantageously comprises at least one step iv) consisting of depositing at least one additional metal selected from platinum, palladium, rhenium, rhodium, ruthenium, manganese and tantalum on said catalyst support. Preferably, said additional metal is selected from platinum, ruthenium and rhenium and highly preferably, said additional metal is platinum. Deposition of at least said additional metal on said support may be carried out using any method known to the skilled person, preferably by impregnation of the catalyst support using at least one solution containing at least one precursor of said additional metal, for example by dry impregnation or by excess impregnation. Said step iv) may be carried out either separately from steps i) and ii) in any order, or simultaneously with said step i) and/or said step ii). More precisely, it may be carried out in association with at least one of the three implementations for the preparation of the catalyst described above. Preferably, said step iv) for depositing at least said additional metal is carried out simultaneously with at least one step i) for depositing at least said metal from group VIII. In accordance with a highly preferred implementation, the catalyst is prepared using a process comprising at least one step for co-impregnation of said metal from group VIII and said organic compound, preferably a cyclodextrin and highly preferably beta-cyclodextrin, and at least one step for co-impregnation of at least said metal from group VIII and at least said additional metal. Said step iv) is preferably followed immediately by at least one drying step then by at least one step for calcining under conditions (temperature, duration) such as those described above.

The catalyst prepared in accordance with at least one of the implementations described above is in the oxide form before being used in the hydrocarbon synthesis process of the invention: the metal(s) from group VIII present in the active phase are in the oxide state and are in the form of crystallites of the oxide of said metal from group VIII with a reduced size. Said catalyst may be entirely or partially free of said organic compound formed from at least one cyclic oligosaccharide composed of at least 6 α-(1,4)-bonded glucopyranose subunits.

Prior to using it in the catalytic reactor and carrying out the process of the invention, the catalyst undergoes at least one reducing treatment, for example with hydrogen, pure or diluted, at high temperature. This treatment means that said catalyst can be activated and form particles of metal, in particular metal from group VIII, in the zero valency state. The temperature of this reduction treatment is preferably in the range 200° C. to 500° C. and its duration is in the range 2 to 20 hours.

This reduction treatment is carried out either in situ (in the same reactor as that in which the Fischer-Tropsch reaction in the process of the invention is being carried out) or ex situ before being loaded into the reactor.

The hydrocarbon synthesis process of the invention is operated at a total pressure in the range 0.1 to 15 MPa, preferably in the range 0.5 to 10 MPa, at a temperature in the range 150° C. to 350° C., preferably in the range 180° C. to 270° C. The hourly space velocity is advantageously in the range 100 to 20000 volumes of synthesis gas per volume of catalyst per hour (100 to 20000 $h^{-1}$) and preferably in the range 400 to 10000 volumes of synthesis gas per volume of catalyst per hour (400 to 10000 $h^{-1}$).

The invention is illustrated in the following examples.

EXAMPLES

The series of catalysts prepared in Examples 1 and 2 were prepared with the same reducible cobalt content, i.e. cobalt in the oxide form which could be reduced to metallic cobalt by a reduction reaction at a temperature of less than 500° C.

Example 1 (Comparative)

Preparation of Catalysts in the Absence of Cyclic Oligosaccharide

Example 1.1

Preparation of Catalyst A1 with Formula $Co/Al_2O_3$

A catalyst A1 comprising cobalt deposited on an alumina support was prepared by dry impregnation of an aqueous solution of cobalt nitrate so as to deposit of the order of 13.5% by weight of Co in two successive steps on a gamma alumina powder (PURALOX SCCa 5/170, SASOL) with a mean grain size of 80 μm, a surface area of 165 $m^2/g$ and a pore volume of 0.477 ml/g.

After a first dry impregnation, the solid was dried in a traversed bed at 120° C. for 3 h in air then calcined at 400° C. for 4 h in a traversed bed in a stream of air. The intermediate catalyst contained approximately 8% by weight of Co. It underwent a second dry impregnation step using a cobalt nitrate solution. The solid obtained was dried in a traversed bed at 120° C. for 3 h in air and calcined at 400° C. for 4 h in a traversed bed in a stream of air. The final catalyst A1 was obtained which contained 13.5% by weight of Co (reducible cobalt).

Example 1.2

Preparation of Catalyst A2 with Formula $Co/Al_2O_3$ in the Presence of saccharose Saccharose or sucrose is a double sugar formed by condensation of 2 oses: one molecule of glucose and one molecule of fructose. It is not a cyclic oligosaccharide. The developed formula of saccharose is given below:

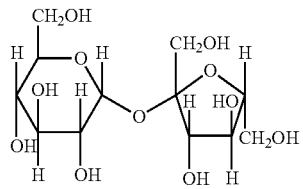

The support for catalyst A2 was identical to that for catalyst A1 described in Example 1.1.

In a first step, an aqueous solution of cobalt nitrate was impregnated into said support. The solid obtained was dried in a traversed bed at 120° C. for 3 hours in air then calcined at 400° C. for 4 hours in a traversed bed to obtain an intermediate catalyst containing a total of 7.6% by weight of Co. In a second step, this intermediate catalyst was impregnated with an aqueous solution containing cobalt nitrate and saccharose (supplied by Sigma-Aldrich, 99% purity, 44 mg of saccharose per gram of catalyst A2 prepared). The solid obtained was dried at 120° C. for 3 hours then calcined at 400° C. for 4 hours. The concentration of Co in each of the cobalt nitrate solutions was adjusted to obtain the catalyst A2 with the desired final Co content. The final catalyst A2 had a total cobalt content of 13.7% by weight (reducible cobalt).

Example 1.3

Preparation of Catalyst B1 with Formula $Co/Al_2O_3.SiO_2$

A catalyst B1 comprising cobalt deposited on a silica-alumina support was prepared by dry impregnation of an aqueous solution of cobalt nitrate so as to deposit of the order of 14% by weight of Co in two successive steps on a silica-alumina initially containing 5% by weight of $SiO_2$ and having a specific surface area of 173 $m^2/g$ and a pore volume of 0.55 ml/g (Siralox 5/170, SASOL).

After a first dry impregnation, the solid was dried in a traversed bed at 120° C. for 3 h in air then calcined at 400° C. for 4 h in a traversed bed in a stream of air. The intermediate catalyst contained approximately 8% by weight of Co. It underwent a second dry impregnation step using a cobalt nitrate solution. The solid obtained was dried in a traversed bed at 120° C. for 3 h in air then calcined at 400° C. for 4 h in a traversed bed. The final catalyst B1 was obtained which contained 13.9% by weight of Co (reducible cobalt).

Example 1.4

Preparation of Catalyst B2 with Formula $Co/CoAl_2O_4$—$Al_2O_3.SiO_2$

A catalyst B2 comprising cobalt deposited on a support based on a spinel included in a silica-alumina was prepared by dry impregnation of an aqueous solution of cobalt nitrate so as to deposit of the order of 13.7% by weight of cobalt onto the support in two successive steps.

The spinel present in the support for catalyst B2 was a simple spinel formed from cobalt aluminate, which was included in a silica-alumina containing 5% by weight of $SiO_2$ and having a specific surface area of 173 $m^2/g$ and a pore volume of 0.55 ml/g (Siralox 5/170, SASOL). The spinel included in the silica-alumina was prepared by dry impregnation of an aqueous cobalt nitrate solution in order to introduce 5% by weight of Co into said silica-alumina. After drying at 120° C. for 3 hours, the solid was calcined at 850° C. for 4 hours in air. The support for catalyst B2 was formed from 5% by weight of cobalt in the form of cobalt aluminate (i.e. 15% by weight of spinel) in the silica-alumina.

The active phase based on cobalt was then deposited on said support in two successive steps, by dry impregnation, using an identical protocol to that described for the preparation of catalyst A1. The steps for drying and calcining were also carried out under the same operating conditions as in Example 1.1. The concentration of cobalt in the cobalt nitrate solution, used for the successive impregnations, was selected so as to obtain the catalyst B2 with the final desired Co content.

The final catalyst B2 had a total cobalt content of 18.7% by weight (including the quantity of Co present in the spinel phase) and a reducible cobalt content of 13.7% by weight.

Example 2 (Invention)

Preparation of Catalysts in the Presence of Cyclic Oligosaccharide (Cyclodextrin)

Example 2.1

Preparation of Catalyst C with Formula Co/CoAl$_2$O$_4$—Al$_2$O$_3$.SiO$_2$

The support for catalyst C was identical to that of catalyst B2 described in Example 1.4. It was prepared in a manner analogous to that indicated in Example 1.4.

In a first step, a solution containing β-cyclodextrin (SIGMA-ALDRICH, 98% purity, 39 mg of β-cyclodextrin per gram of prepared catalyst C) was deposited on said support by dry impregnation. The solid was then dried in air in a traversed bed type reactor for 3 hours at 120° C. Deposition of the active phase based on Co was then carried out in two successive steps, by dry impregnation, following the same protocol as that given for catalyst B2. The concentration of cobalt in the cobalt nitrate solution used for the successive impregnations was selected to obtain the catalyst C with the desired final Co content.

The final catalyst C had a total cobalt content of 18.8% by weight (including the Co content present in the spinel phase) and a reducible cobalt content of 13.7% by weight.

Example 2.2

Preparation of Catalyst D with Formula Co/CoAl$_2$O$_4$—Al$_2$O$_3$.SiO$_2$

The support for catalyst D was identical to that of catalyst B2 described in Example 1.4. It was prepared in a manner analogous to that indicated in Example 1.4.

In a first step, an aqueous solution containing cobalt nitrate and β-cyclodextrin (SIGMA-ALDRICH, 98% purity, 26 mg of β-cyclodextrin per gram of catalyst D prepared) was impregnated on said support (co-impregnation step). The solid obtained was dried in a traversed bed at 120° C. for 3 hours in air then calcined at 400° C. for 4 hours in a traversed bed to obtain an intermediate catalyst containing a total of 13% by weight of Co (including the Co content present in the spinel phase). It underwent a second dry impregnation step using a cobalt nitrate solution. The solid obtained was dried in a traversed bed at 120° C. for 3 h in air then calcined at 400° C. for 4 h in a traversed bed. The concentration of Co in each of the cobalt nitrate solutions was selected to obtain the catalyst D with the desired final Co content.

The final catalyst D had a total cobalt content of 18.9% by weight (Co content present in the spinel phase included) and a reducible cobalt content of 13.7% by weight.

Example 2.3

Preparation of Catalyst E with Formula Co/CoAl$_2$O$_4$—Al$_2$O$_3$.SiO$_2$

The support for catalyst E was identical to that of catalyst B2 described in Example 1.4. It was prepared in a manner analogous to that indicated in Example 1.4.

In a first step, an aqueous solution of cobalt nitrate was impregnated on said support. The solid obtained was dried in a traversed bed at 120° C. for 3 hours in air then calcined at 400° C. for 4 hours in a traversed bed to obtain an intermediate catalyst containing a total of 12.9% by weight of Co (including the Co content present in the spinel phase). In a second step, this intermediate catalyst was impregnated with an aqueous solution containing cobalt nitrate and β-cyclodextrin (SIGMA-ALDRICH, 98% purity, 37 mg of β-cyclodextrin per gram of catalyst E prepared). The solid obtained was dried at 120° C. for 3 hours then calcined at 400° C. for 4 h. The concentration of Co in each of the cobalt nitrate solutions was selected to obtain the catalyst E with the desired final Co content.

The final catalyst E had a total cobalt content of 19.0% by weight (Co content present in the spinel phase included) and a reducible cobalt content of 13.9% by weight.

Example 2.4

Preparation of Catalyst F with Formula Co/CoAl$_2$O$_4$—Al$_2$O$_3$.SiO$_2$

The support for catalyst F was identical to that of catalyst B2 described in Example 1.4. It was prepared in a manner analogous to that indicated in Example 1.4.

A solution containing β-cyclodextrin (SIGMA-ALDRICH, 98% purity, 37 mg of β-cyclodextrin per gram of catalyst F prepared) was deposited by post-treatment on a catalyst prepared using the same conditions as catalyst B2. The solid obtained was then dried in a traversed bed type reactor at 120° C. for 3 hours in a stream of air.

The final catalyst F had a total cobalt content of 18.7% by weight (Co content present in the spinel phase included) and a reducible cobalt content of 13.7% by weight.

Example 2.5

Preparation of Catalyst G with Formula Co(Pt)/CoAl$_2$O$_4$—Al$_2$O$_3$.SiO$_2$

The support for catalyst G was identical to that of catalyst B2 described in Example 1.4. It was prepared in a manner analogous to that indicated in Example 1.4.

In a first step, an aqueous solution containing cobalt nitrate and β-cyclodextrin (SIGMA-ALDRICH, 98% purity, 26 mg of β-cyclodextrin per gram of catalyst G prepared) was impregnated into said support (co-impregnation step). The solid obtained was dried in a traversed bed at 120° C. for 3 hours in air then calcined at 400° C. for 4 hours in a traversed bed to obtain an intermediate catalyst containing a total of 13% by weight of Co (including the Co content present in the spinel phase). It underwent a second co-impregnation step using an aqueous solution containing cobalt nitrate and tetraamine platinum hydroxide with formula [Pt(NH$_3$)$_4$](OH)$_2$. The solid obtained was dried at 120° C. for 3 h in dry air then calcined at 400° C. for 4 h in dry air. The concentration of Co in each of the cobalt nitrate solutions and that of platinum in the tetraamine platinum hydroxide solution were selected to obtain the catalyst G with the desired final Co and Pt contents.

The final catalyst G had a platinum content of 0.0545% by weight, a total cobalt content of 18.9% by weight (Co content present in the spinel phase included) and a reducible cobalt content of 13.8% by weight.

Example 2.6

Preparation of Catalyst H with Formula Co/Al$_2$O$_3$

The support for catalyst H was identical to that of A1.

In a first step, an aqueous solution of cobalt nitrate was impregnated onto said support. The solid obtained was dried in a traversed bed at 120° C. for 3 hours in air then calcined at 400° C. for 4 hours in a traversed bed to obtain an intermediate catalyst containing a total of 7.5% by weight of Co. In a second step, this intermediate catalyst was impregnated with an aqueous solution containing cobalt nitrate and β-cyclodextrin (SIGMA-ALDRICH, 98% purity, 24 mg of β-cyclodextrin per gram of catalyst H prepared). The solid obtained was dried at 120° C. for 3 h then calcined at 400° C. for 4 h. The concentration of Co in each of the cobalt nitrate solutions was selected to obtain the catalyst H with the desired final Co content.

The final catalyst H had a total cobalt content of 13.7% by weight (reducible Co).

Example 2.7

Preparation of Catalyst I with Formula Co/Al$_2$O$_3$.SiO$_2$

The support for catalyst I was identical to that of catalyst B1 described in Example 1.3.

In a first step, an aqueous solution containing cobalt nitrate and β-cyclodextrin (SIGMA-ALDRICH, 98% purity, 26 mg of β-cyclodextrin per gram of catalyst I prepared) was impregnated on said support (co-impregnation step). The solid obtained was dried in a traversed bed at 120° C. for 3 hours in air then calcined at 400° C. for 4 hours to obtain an intermediate catalyst containing a total of 6.7% by weight of Co. It underwent a second dry impregnation step using a cobalt nitrate solution. The solid obtained was dried in a traversed bed at 120° C. for 3 h in air then calcined at 400° C. for 4 h in a traversed bed. The concentration of Co in each of the cobalt nitrate solutions was selected to obtain the catalyst I with the desired final Co content.

The final catalyst I had a total cobalt content of 13.7% by weight (reducible Co).

Table 1 below summarizes the total cobalt contents of each final catalyst, the quantities of organic compound introduced per gram of catalyst (β-cyclodextrin or saccharose), the molar ratio Co$_{total}$/organic compound and the molar ratio Co$_{reducible\ (no\ spinel)}$/organic compound, the organic compound being β-cyclodextrin for catalysts C to I and saccharose for catalyst A2.

TABLE 1

Co content and organic compound content for each catalyst

| Catalyst | Total wt % of cobalt | % by weight of organic compound | Molar ratio Co$_{total}$/organic compound (1) | Molar ratio Co$_{reducible\ (no\ spinel)}$/organic compound (2) |
|---|---|---|---|---|
| A1 (comparative) | 13.5 | — | — | — |
| A2 (comparative) | 13.7 | 4.4 | 18 | 18 |
| B1 (comparative) | 13.9 | — | — | — |
| B2 (comparative) | 18.7 | — | — | — |
| C (invention) | 18.8 | 3.9 | 92 | 69 |
| D (invention) | 18.9 | 2.6 | 139 | 104 |
| E (invention) | 19.0 | 3.7 | 106 | 79 |
| F (invention) | 18.7 | 3.7 | 105 | 78 |
| G (invention) | 18.9 | 2.6 | 139 | 104 |
| H (invention) | 13.7 | 2.4 | 108 | 108 |
| I (invention) | 13.7 | 2.6 | 103 | 103 |

(1): the cobalt content used to calculate the molar ratio Co$_{total}$/organic compound, in particular the molar ratio Co$_{total}$/β-cyclodextrin, is that resulting not only from the cobalt present in the spinel phase of the support but also the cobalt in the oxide form present in the active phase of the catalyst and introduced via the various support impregnation steps.
(2): the cobalt content used to calculate the molar ratio Co$_{reducible\ (no\ spinel)}$/organic compound, in particular the molar ratio Co$_{reducible\ (no\ spinel)}$/β-cyclodextrin, is that linked to the cobalt in the oxide form present in the active phase of the catalyst and introduced onto the support via the various impregnation steps. It does not take into account the cobalt present in the spinel phase of the support.

Example 3

Dispersion of Cobalt Present in the Comparative Catalysts A1, A2, B1 and B2 and in the Catalysts C, D, E, G, H and I in Accordance with the Invention In this example, the dispersion of cobalt was characterized firstly by determining the mean size of the crystallites of cobalt oxide (Co$_3$O$_4$) present in each of the catalysts. The mean size of the crystallites of cobalt oxide was determined by X ray diffraction from the Scherrer equation for the diffraction peak at 59.5° (511 plane). The diameter of the Co$_3$O$_4$ crystallites is expressed in nanometers (nm). For each catalyst, the size of the crystallites, expressed by their diameter, is shown in Table 2.

The dispersion of the cobalt was also characterized by a complementary method based on the chemisorption of propene which was carried out using a pulse of propene with a volume of 50 μL at 50° C. in a stream of helium. In this method, described in more detail in the publication by A S Lermontov, J S Girardon, A Griboval-Constant, D Pietrzyk and A Y Khodakov, Catalysis Letters 101 (2005), 117, each catalyst was previously reduced in a stream of hydrogen at 400° C. for 10 hours and with an hourly space velocity (HSV) of 12500 h$^{-1}$. The results are expressed in micromoles of propene chemisorbed per gram of reducible cobalt of the catalyst. For each catalyst, the quantity of chemisorbed propene is presented in Table 2.

TABLE 2

Characterization of dispersion of cobalt for each catalyst

| Catalyst | Total wt % of cobalt | % by weight of β-cyclodextrin or saccharose | Co$_3$O$_4$ crystallite size (nm) | Chemisorbed propene (μmoles/g of reducible Co) |
|---|---|---|---|---|
| A1 (comparative) | 13.5 | 0.0 | 12.4 | 140.0 |
| A2 (comparative) | 13.7 | 4.4 | 11.0 | 137.8 |
| B1 (comparative) | 13.9 | 0.0 | 12.8 | 140.3 |
| B2 (comparative) | 18.7 | 0.0 | 12.3 | 146.0 |
| C (invention) | 18.8 | 3.9 | 7.5 | 176.6 |
| D (invention) | 18.9 | 2.6 | 7.9 | 193.4 |

TABLE 2-continued

Characterization of dispersion of cobalt for each catalyst

| Catalyst | Total wt % of cobalt | % by weight of β-cyclodextrin or saccharose | $Co_3O_4$ crystallite size (nm) | Chemisorbed propene (μmoles/g of reducible Co) |
|---|---|---|---|---|
| E (invention) | 19.0 | 3.7 | 11.0 | 159.0 |
| G (invention) | 18.9 | 2.6 | 7.6 | 240.6 |
| H (invention) | 13.7 | 2.4 | 10.2 | 157.6 |
| I (invention) | 13.7 | 2.6 | 8.2 | 180.3 |

By comparing the catalysts flaying identical supports (H for A1 and A2; I for B1; C, D, E and G for B2), the results show that the catalysts prepared in the presence of cyclodextrin have a mean $Co_3O_4$ crystallite size which is significantly smaller than that of the catalysts prepared in the absence of organic compound or in the presence of a non-cyclic oligosaccharide (saccharose used for catalyst A2). This size varies as a function of the mode in which the β-cyclodextrin is used and of the quantity introduced. It also appears that the quantity of chemisorbed propene appears to be linked to this size of crystallites. The results shown in Table 2 show that the smaller the size of the crystallites, the larger is the quantity of chemisorbed propene, which indicates an increased in the number of active sites, not only because of the increase in the number of $Co_3O_4$ crystallites but also of the good reducibility of cobalt. The results shown in Table 2 demonstrate that the catalyst D, prepared by co-impregnation of beta-cyclodextrin and cobalt, resulted in very good dispersion of cobalt and a high quantity of chemisorbed propene. The catalyst G, also prepared by co-impregnation of beta-cyclodextrin and cobalt and comprising platinum in its composition, produced better results.

Example 4

Catalytic Performances of Catalysts A1, A2, B1, B2, C, D, E, F, G, H and I in Synthesis Gas Conversion Catalysts A1, A2, B1, B2, C, D, E, F, G, H and I, before being tested in succession in synthesis gas conversion, were reduced in situ in a stream of pure hydrogen at 400° C. for 16 hours. The Fischer-Tropsch synthesis reaction was carried out in a fixed bed type tube reactor operating continuously.

Each of the catalysts was in the form of a powder with a diameter in the range 40 to 150 microns.

The test conditions were as follows:
Temperature=220° C.;
Total pressure=2 MPa;
hourly space velocity (HSV)=5000 $h^{-1}$;
$H_2$/CO molar ratio=2/1.

The results, expressed in terms of activity (rate of CO consumption) and productivity, are shown in Table 3.

TABLE 3

Catalytic performances of each catalyst

| Catalyst | Rate of CO consumption ($10^{-1}g \cdot h^{-1} \cdot g_{cats}^{-1}$) after 60 h in reaction stream | Productivity, by weight of C5+ ($g \cdot h^{-1} \cdot g_{cats}^{-1}$) |
|---|---|---|
| A1 (comparative) | 5.2 | 0.46 |
| A2 (comparative) | 4.8 | 0.41 |
| B1 (comparative) | 6.1 | 0.55 |
| B2 (comparative) | 6.6 | 0.57 |
| C (invention) | 14.7 | 1.26 |

TABLE 3-continued

Catalytic performances of each catalyst

| Catalyst | Rate of CO consumption ($10^{-1}g \cdot h^{-1} \cdot g_{cats}^{-1}$) after 60 h in reaction stream | Productivity, by weight of C5+ ($g \cdot h^{-1} \cdot g_{cats}^{-1}$) |
|---|---|---|
| D (invention) | 19.5 | 1.46 |
| E (invention) | 11.0 | 0.91 |
| F (invention) | 7.2 | 0.65 |
| G (invention) | 25.8 | 2.27 |
| H (invention) | 5.9 | 0.53 |
| I (invention) | 18.9 | 1.42 |

By comparing the catalysts having identical supports (H for A1 and A2; I for B1; C, D, E, F and G for B2), the results shown in Table 3 demonstrate that the catalysts prepared in the presence of cyclodextrin are much more active than the catalysts prepared in the absence of a cyclic oligosaccharide. Further, the catalysts prepared in the presence of cyclodextrin result in a productivity for the desired C5+ products greater than that obtained using the catalysts prepared in the absence of a cyclic oligosaccharide. The catalysts prepared in the presence of cyclodextrin are thus more selective for the desired products. The improvement in the catalytic performances in terms of activity and productivity can be appreciated by comparing the catalyst A2 (prepared using saccharose) with catalyst H (prepared using beta-cyclodextrin): the preparation of a catalyst using beta-cyclodextrin, which is a cyclic oligosaccharide, results in the production of a catalyst which is more active and more selective for the desired C5+ products than a catalyst prepared using an organic compound which does not belong to the cyclic oligosaccharide family.

The invention claimed is:

1. A process for synthesizing essentially linear, saturated C5+hydrocarbons, consisting of bringing a feed comprising synthesis gas into contact with at least one catalyst the active phase of which comprises at least one metal from group VIII deposited on a support formed by at least one oxide, said catalyst being prepared using a process comprising at least:
    i) at least one step for bringing at least said support into contact with at least one solution containing at least one precursor of said metal from group VIII;
    ii) at least one step for bringing at least said support into contact with at least one organic compound formed from at least one cyclic oligosaccharide composed of at least 6 α-(1,4)-bonded glucopyranose subunits;
    iii) at least one calcining step to obtain at least said metal from group VIII in the oxide form;
    the steps i) and ii) possibly being carried out separately, in any order, or simultaneously.

2. A hydrocarbon synthesis process according to claim 1, in which said active phase comprises cobalt.

3. A hydrocarbon synthesis process according to claim 1, in which said active phase comprises at least one additional metal selected from platinum, palladium, rhenium, ruthenium, manganese and tantalum.

4. A hydrocarbon synthesis process according to claim 1, in which said catalyst contains crystallites of oxide of said metal from group VIII with a mean diameter of at least 6 nm.

5. A hydrocarbon synthesis process according to claim 1, in which said support is formed by at least one simple oxide selected from alumina ($Al_2O_3$), silica ($SiO_2$), titanium oxide ($TiO_2$), cerine ($CeO_2$) and zirconia ($ZrO_2$).

6. A hydrocarbon synthesis process according to claim 1, in which said support is formed from a spinel included in an alumina or a silica-alumina.

7. A hydrocarbon synthesis process according to claim 1, in which said organic compound is selected from cyclodextrins, substituted cyclodextrins, polymerized cyclodextrins and a mixture of cyclodextrins.

8. A hydrocarbon synthesis process according to claim 7, in which the cyclodextrins are α-cyclodextrin, β-cyclodextrin and γ-cyclodextrin respectively composed of 6, 7 and 8 α-(1, 4)-bonded glucopyranose subunits.

9. A hydrocarbon synthesis process according to claim 7, in which the substituted cyclodextrins are hydroxypropyl beta-cyclodextrin and methylated beta-cyclodextrins.

10. A hydrocarbon synthesis process according to claim 1, in which said organic compound for carrying out said step ii) is introduced such that the molar ratio { (metal(s) from group VIII in the oxide form present in the active phase of the catalyst obtained from said step iii)/organic compound} is in the range 10 to 300.

11. A hydrocarbon synthesis process according to claim 1, in which when said steps i) and ii) are carried out simultaneously, the catalyst preparation comprises carrying out one or more steps i).

12. A hydrocarbon synthesis process according to claim 1, in which said step i) is carried out prior to said step ii).

13. A hydrocarbon synthesis process according to claim 1, in which said step ii) is carried out prior to said step i).

14. A hydrocarbon synthesis process according to claim 1, in which said calcining step iii) is carried out at a temperature in the range 200° C. to 800° C.

15. A hydrocarbon synthesis process according to claim 1, which is operated at a total pressure in the range 0.1 to 15 MPa, at a temperature in the range 150° C. to 350° C., the hourly space velocity being in the range 100 to 20000 volumes of synthesis gas per volume of catalyst per hour (100 to 20000 $h^{-1}$).

* * * * *